United States Patent [19]
Lee et al.

[11] Patent Number: 5,560,937
[45] Date of Patent: Oct. 1, 1996

[54] METHOD FOR PURIFICATION OF CARDIAC TROPONIN I

[75] Inventors: Lillian Lee, North York; George Jackowski, Inglewood, both of Canada

[73] Assignee: Spectral Diagnostics, Inc., Toronto, Canada

[21] Appl. No.: 296,644

[22] Filed: Aug. 26, 1994

Related U.S. Application Data

[63] Continuation-in-part of Ser. No. 110,824, Aug. 24, 1993, abandoned.

[51] Int. Cl.⁶ .................................................. A61K 35/34
[52] U.S. Cl. ........................... 424/569; 514/2; 514/21; 530/350; 530/412; 530/414; 530/417; 530/814
[58] Field of Search ................... 424/569; 514/2, 514/21; 530/350, 412, 414, 417, 814

[56] References Cited

PUBLICATIONS

Rosenthal et al., Biochemical Pharmacology 42(3):685–692 (1991).
Jin et al., J. Biol. Chem. 263(15):7309–7315 (1988).
Beier et al., Eur J. Biochem. 176:327–334 (1988).
Tang et al., Shengwn Huaxue Zazhi 8(3):267–71 (1992) (Abstract).
Sugita et al., Muscle Nerve 3(4):335–339 (1980).

*Primary Examiner*—Chhaya D. Sayala
*Assistant Examiner*—Jean C. Witz
*Attorney, Agent, or Firm*—Klauber & Jackson

[57] ABSTRACT

A method is provided for isolating substantially intact cardiac troponin I from cardiac tissue comprising extracting the troponin I and purifying it in the presence of an effective mount of a mixture of protease inhibitors. The human cardiac troponin I, prepared by the present method is characterised by a molecular weight of about 28 kDa.

13 Claims, 4 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
    ( A ) LENGTH: 31 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:1:

```
Ala Asp Gly Ser Ser Asp Ala Ala Arg Glu Pro Arg Pro Ala Pro Ala
 1               5                  10                  15
Pro Ile Arg Arg Arg Ser Ser Asn Tyr Arg Ala Tyr Ala Thr Glu
            20                  25                  30
```

METHOD FOR PURIFICATION OF CARDIAC TROPONIN I

This is a continuation-in-pan application of U.S. application Ser. No. 08/110,824, filed Aug. 24, 1993 now abandoned.

FIELD OF THE INVENTION

This invention relates to methods for purifying troponins. More particularly, this invention relates to methods for the purification of intact cardiac troponin I with improved stability and the cardiac troponin I so produced.

BACKGROUND OF THE INVENTION

Detection and measurement of human cardiac troponin I (cTnI) in serum has been proposed as a sensitive early indicator of myocardial infarction (Larue et al., (1992), Molec. Immunol. v. 29, pp. 271–278 and (1993), Clin. Chem. v. 39, pp. 972–979; Bodor et al., (1992), Clin. Chem., v. 38, pp. 2203–2214). For reproducible and reliable clinical testing, stable calibration standards and quality control standards are required. Such standards require pure and stable preparations of intact human cardiac troponin I.

cDNA coding for human cTnI has been cloned and sequenced (Vallins et al., (1990), FEBS Letters, v. 270, pp. 57–61; Hunkeler et al., (1991), Circ. Res., v. 69, pp. 1409–1414). The cDNA indicates an amino acid sequence of 210 amino acids or a molecular weight of approximately 28 kDa. Purified preparation of cTnI, however, have been reported to have molecular weights of 22.5 kDa (Lame et al. (1992); Bodor et al. (1992)), suggesting a loss of pan of the molecule.

Furthermore, previously described methods for the isolation and purification of cTnI (Tsukui et al., (1973), J. Biochem. v. 73, pp. 1119–1121; Cummins et al., (1978), Biocem. J. v. 171, pp. 251–259; Syska et al. (1974), FEBS Lett. v. 40, pp. 253–257) yielded preparations which were unstable and subject to considerable degradation on storage.

Protease inhibitors have been suggested for use in the purification of cardiac troponins, but generally only one or two inhibitors were used (Beier et al., (1988), Eur. J. Biochem., v. 176, pp. 327–334; Jin et al., (1988), J. Biol. Chem. v. 263, p. 7309; Stull et al., (1977), J. Biol. Chem. v. 252, pp. 851–857).

Beier et al., (1988), used phenylmethylsulphonyl fluoride ($PhMeSO_2F$) and benzamidine as inhibitors during the extraction and isolation of troponin from bovine heart tissue. This purification method involved an extraction with high salt (LiCl) followed by ammonium sulfate (($NH_4)_2SO_4$) precipitation and DEAE-cellulose column chromatography. Jin et al., (1988), used phenylmethanesulphonyl fluoride (PMSF) in their extraction procedure for the purification of cardiac troponin T from beef heart. This purification method included a 60° C. treatment of a high salt (KCl) extract, ammonium sulfate fractionation and DEAE-cellulose column chromatography. Stull et al., (1977), also used PMSF in their extraction procedure for isolating troponin complex containing both troponin C, troponin I, and troponin T from beef hearts. This purification procedure involved ethanol extraction, ether wash, high salt treatment with 1 M KCl, ammonium surfate fractionation and column chromatography with a Bio-Gel sepharose column and hydroxylapatite chromatography.

There remains a need for a method for purifying cTnI which will protect the integrity of the molecule and yield cTnI preparations which can meet the stringent stability requirements for clinical assay standards and calibrators.

SUMMARY OF THE INVENTION

The present invention is directed to a method for purifying substantially intact cardiac troponin I with improved stability. According to the present invention, it has been found that the isolation and purification of cardiac troponin I in the presence of a mixture of protease inhibitors, results in a purified cardiac troponin I with improved stability and having a molecular weight of about 28 kDa, which is higher than in previously reported purified preparations.

The protease inhibitor mixture according to the present invention is effective to inhibit degradation of the protein, so that a substantial mount of the cardiac troponin I isolated is intact cardiac troponin I, having a molecular weight of about 28 kDa. Specifically, the protease inhibitor mixture of the present invention is effective to inhibit degradation of the cardiac specific N-terminal region of cardiac troponin I.

The protease inhibitor mixture of the present invention comprises at least 2 different cathepsin protease inhibitors, a serine protease inhibitor and a cysteine protease inhibitor. The protease inhibitor mixture can also contain an aspmate protease inhibitor, an aminopeptidase inhibitor or a metal-loendo-peptidase inhibitor.

According to the present invention there is provided a method of isolating a pure, stable cardiac troponin I preparation, the troponin I having a molecular weight of about 28 kDa which comprises the steps of: extracting human cardiac tissue with an aqueous extraction buffer at a pH of from about 7 to 9 which is 8 to 10 M in Urea and contains a protease inhibitor mixture comprising at least two cathepsin protease inhibitors, at least one serine protease inhibitor and at least one cysteine protease inhibitor; separating the troponin I from the extract by affinity chromatography in the presence of the extraction buffer and calcium ion thereby to absorb the troponin I; and desorbing the troponin I by washing with the aqueous extraction buffer containing EGTA.

In a further embodiment of the present invention, the protease inhibitor mixture can further contain an aspartate protease inhibitor, an aminopeptidase inhibitor or a metal-loendo-peptidase inhibitor.

Accordingly, a mixture of protease inhibitors which can be used according to the present invention include leupeptin, pepstatin, PMSF and E-64.

According to the present invention there is further provided a pure, stable cardiac troponin I preparation, the troponin I having a molecular weight of about 28 kDa, prepared by a process which comprises the steps of: extracting human cardiac tissue with an aqueous extraction buffer at a pH of from about 7 to 9 which is 8 to 10 M in Urea and contains a protease inhibitor mixture comprising at least two cathepsin protease inhibitors, at least one serine protease inhibitor and at least one cysteine protease inhibitor; separating the troponin I from the extract by affinity chromatography in the presence of the extration buffer and calcium ion thereby to absorb the troponin I; and desorbing the troponin I by washing with the aqueous extraction buffer containing EGTA.

BRIEF DESCRIPTION OF THE DRAWINGS

The invention, as exemplified by a preferred embodiment, is described with reference to the accompanying drawings, in which:

FIG. 4 shows the stability at room temperature (RT) of human cTnI prepared by the method of the invention, wherein;

Panel A:
  Lane 1: cTnI stored 1 week at RT,
  Lane 2: control preparation stored at –20° C., and
  Lane 3: Molecular weight standards (as in FIG. 1);

Panel B:
  Lane 1: cTnI stored 3 weeks at RT,
  Lane 2: control preparation stored at –20° C., and
  Lane 3: Molecular weight standards (as in FIG. 1);

Panel C:
  Lane 1: cTnI stored 5 weeks at RT,
  Lane 2: control preparation stored at –20° C., and
  Lane 3: Molecular weight standards (as in FIG. 1).

DETAILED DESCRIPTION OF THE INVENTION

Previously reported purified human cTnI preparations had molecular weights of 24 kDa (Cummins et al., (1978), Biochem. J., v. 171, pp. 251–259; Grand et al., (1976), Biochem. J., v. 159, pp.. 633–641) and 22.5 kDa (Larue (1989); Bodor (1989)).

Sequencing of the cDNA for human cTnI indicates a protein of 210 amino acids. If the protein is 6% glycosylated and assuming an amino acid average molecular weight of 125, the molecular weight of human cardiac troponin I should be approximately 27.8 kDa.

Figure 2:
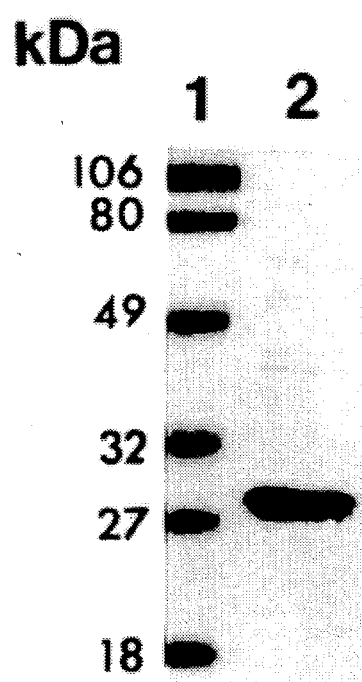
FIG. 2 shows the results of SDS-PAGE gel analysis of a preparation of human cTnI in accordance with the invention, wherein, Lane 1: molecular weight standards: phosphorylase B (106 kDa); bovine serum albumin (80 kDa); ovalbumin (49 kDa); carbonic anhydrase (32 kDa); soybean trypsin inhibitor (27 kDa) and lysozyme (18 kDa), and Lane 2: human cTnI prepared by the method of the invention.

The present inventors have found that if a mixture of protease inhibitors is employed during isolation of cardiac troponin I, both during the extraction stage and during subsequent purification, substantially intact cardiac troponin I of a molecular weight of approximately 28 kDa is obtained, as demonstrated by SDS-PAGE gel electrophoresis, and as shown in FIG. 2.

The protease inhibitor mixture according to the present invention is effective to inhibit degradation so that a substantial amount of the cardiac troponin I isolated is intact cardiac troponin I having a molecular weight of about 28 kDa. Specifically the protease inhibitor mixture of the present invention is effective to inhibit degradation of the cardiac specific N-terminal region of cardiac troponin I. This region can include the 31 amino acid N-terminal sequence of cardiac troponin I (SEQ ID NO: 1), which is as follows:

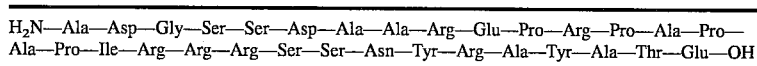

H₂N—Ala—Asp—Gly—Ser—Ser—Asp—Ala—Ala—Arg—Glu—Pro—Arg—Pro—Ala—Pro—
Ala—Pro—Ile—Arg—Arg—Arg—Ser—Ser—Asn—Tyr—Arg—Ala—Tyr—Ala—Thr—Glu—OH

The protease inhibitor mixture of the present invention comprises at least two different cathepsin protease inhibitors, a serine protease inhibitor and a cysteine protease inhibitor. The protease inhibitor mixture can also contain an aspartate protease inhibitor, an amino peptidase inhibitor or a metalloendo-peptidase inhibitor. There are a number of protease inhibitors available which have a broad spectrum of activity and therefore, these are useful in the present invention for they will inhibit a number of different types of proteases. A list of protease inhibitors, which can be used according to the present invention, and the specificity of the inhibitors are listed in Table 1. Other inhibitors, which would be known to persons skilled in the art, can also be used according to the present invention.

TABLE 1

| Inhibitor | Specificity of Inhibitor | Suggested Working Concentration |
|---|---|---|
| Aprotinin | Serine protease inhibitor. Does not act on thrombin or Factor Xa. Inhibits plasmin, kallikrein, trypsin, chymotrypsin with high activity. | 0.6–2.0 µg/ml (0.01–0.3 µM) |
| Bestatin | Primarily, if not exclusively, an inhibitor of aminopeptidases (e.g., aminopeptidase B, leucine aminopeptidase, tripeptide aminopeptidase, aminopeptidases on the surface of mammalian cells). It does not inhibit carboxypeptidases. | 40 µg/ml (130 µM) |
| 3,4,-Dichloroisocoumarin | Inhibits a large number of serin proteases such as elastase, cathepsin G and endoproteinase Glu—C. | 1–43 µg/ml (5–200) µM) |
| N-[N-(L,3-trans-carboxy-oxiram-2-carbonyl)-L-leucyl]-agmatine (E-64) | Inhibits papain and other thiolproteases like cathepsin B and L and cysteine proteases. | 0.5–1.0 µg/ml (1.4–2.8 µM) |
| Leupeptin | Inhibits serine and thiol proteases such as trypsin, papain, plasmin and cathepsin B. | 0.5 µg/ml (1 µM) |
| Pepstatin | Inhibits acid proteases such as pepsin, renin, cathepsin D, chymosin, aspartate and many microbial acid proteases. | 0.7 µg/ml (1 µM) |
| Phenylmethanesulfonyl fluoride (PMSF) | Inhibits serine proteases (chymotrypsin, trypsin and thrombin). Also inhibits thiolproteases such as papain (reversible by DTT treatment). | 17–174 µg/ml (100–1000 µM) |
| Aprotinin | Serine protease inhibitor. Does not act on thrombin or Factor Xa. Inhibits plasmin, kallikrein, trypsin, chymotrypsin with high activity. | 0.6–2.0 µg/ml (0.01–0.3 µM) |
| Bestatin | Primarily, if not exclusively, an inhibitor of aminopeptidases (e.g., aminopeptidase B, leucine aminopeptidase, tripeptide aminopeptidase, aminopeptidases on the surface of mammalian cells). It does not inhibit carboxypeptidases. | 40 µg/ml (130 µM) |
| Phosphoramidon | Specifically inhibits thermolysin, collagenase and metalloendoproteinases from various microorganisms (*Bacillus subtilus*, *Streptomyces griseus* and *Pseudomonas aeruginosa*). | 4–330 µg/ml (100–135 µM) |
| Antipain | serine protease inhibitor inhibit trypsin-like enzymes | 50 µg/ml |
| Chymostatin | inhibits serine proteases and inhibits chromotrypsin-like enzymes | 0.1 ng/ml |

In the present invention, at least 2, and in some embodiments, 3 cathepsin inhibitors were used. It was found advisable to use at least two different types of cathepsin inhibitors due to the abundance of cathepsin proteases in cardiac tissue. In one example of the present invention the cathepsin inhibitors used were leupeptin and pepstatin. These two inhibitors will inhibit other groups of proteases besides the cathepsins. As noted from Table 1, leupeptin also inhibits serine and thiol proteases such as trypsin, papain and plasmin. Pepstatin in addition to inhibiting cathepsin D, also inhibits acid proteases such as pepsin, renin; chymosin, aspmate and many microbial acid peptidases.

If a third cathepsin inhibitor is to be added, E-64 is preferred, as this protease will inhibit not only cathepsin B and L, but other thiolproteases like cysteine proteases and papain. An additional cathepsin inhibitor, which is useful according-to the present invention, is 3,4-dichloroisocoumarin. This protease inhibitor inhibits cathepsin G, which is not covered by any of the other cathepsin inhibitors and, therefore, it sometimes can be useful to include in the protease mixture of the present invention. This protease inhibitor also inhibits elastase and endoproteinase Glu-C.

Despite the fact that the cathepsin protease inhibitors may also have some activity against cysteine or serine proteases, a further cysteine protease inhibitor and serine protease inhibitor should also be added to the protease inhibitor mixture of the present invention.

The serine protease inhibitors are important to include in the protease inhibitor mixture as the cardiac specific 31 amino acid N-terminal end contains two sensitive phosphorylation sites at position 22 and 23, a serine amino acid occurring at these positions. The serine protease inhibitor which is used in one embodiment of the present invention is PMSF. This inhibitor is effective against serine proteases such as chymotrypsin, trypsin and thrombin. It also inhibits thiolproteases such as papain. Other serine proteases which can be used according to the present invention include antipain, aprotatin, leupeptin and chymostatin. Antipain inhibits serine proteases such as trypsin-like enzymes. Aprotinin inhibits plasmin, kallikrein, trypsin and chymotrypsin. The other protease inhibitors have been previously discussed in detail.

As mentioned above, a further example of a suitable cysteine protease inhibitor includes E-64.

Accordingly, a mixture of protease inhibitors which can be used according to the present invention include the following: leupeptin, pepstatin, PMSF and E-64.

As noted previously, pepstatin is also an effective aspartate protease inhibitor.

If an aminopeptidase inhibitor is to be included within the protease inhibitor mixture, this aminopeptidase inhibitor could be bestatin. Bestatin inhibits aminopeptidases such as aminopeptidase B, leucine aminopeptidase and aminopeptidases on the surface of mammalian cells.

If a metalloendopeptidase is included within the protease inhibitor mixture, phosphoramidon is suitable. Phosphoramidon inhibits thermolysin, collagenase and metalloendoproteinases from various micro-organisms.

As can be appreciated from the above discussion of the protease inhibitors, a number protease inhibitor mixtures are effective in inhibiting degradation of cardiac troponin I, specifically the N-terminal region of the cardiac troponin I. A suitable choice of an effective protease inhibitor mixture, which can be used according to the teaching of the present invention, will be readily realized by a person skilled in the art.

The protease inhibitor mixtures of the present invention are maintained in a high molar concentration of urea. An 8–10 M Urea solution was found to be effective. The concentration of the urea is maintained at this high level throughout the isolation procedure to ensure inactivation of enzymes capable of phosphorylating or dephosphorylating the cardiac troponin I. Specifically, the Urea will protect the phosphorylation sites at serine 22 and serine 23. If these sites are phosphorylated, they will not be cleaved by proteases. For convenience, a 9 M Urea solution was used throughout the extraction and purification procedure.

It is preferred that the urea should be ultra pure, in that it be free of ammonia and cyanate. Ammonia and cyanate will react with the N-terminal region of the protein and block this region, as is known in the art (A Practical Guide to Protein and Peptide Purification for Microsequencing, Editor Paul T. Matsudaira, Academic Press, 1989). It is well known to persons skilled in the art that a protein blocked at the N-terminal should be avoided. This type of protein may not be amenable for making antibodies, specifically cardiac specific antibodies, as the cardiac specificity is at the N-terminal region. Furthermore, if a blocked protein were used as a standard for calibration curves, a lower signal would result when reacted with an antibody. This is particularly important if the antibody has been specifically raised against the cardiac specific portion of the troponin I. The antibody will not be able to readily bind to the troponin I if the N-terminus is blocked. Ultra pure urea can be obtained from many sources, for example, Bethesda Research Laboratories, in Bethesda Md.

Table 1 provides suggested working concentrations for the protease inhibitors, which are also acceptable for use according to the present invention. Typically a 100 fold stock solution of each inhibitors were prepared and each of the protease inhibitors were used in the range of 0.25 mg/L to 1 mg/L, accept for PMSF, which is used at a concentration ranging from 0.05 mM to 2 mM. The presence and concentration levels of the protease inhibitors were maintained during all stages of troponin I extraction and isolation. At a concentration of approximately 1 mg/L and 2 mM PMSF, substantially all the cardiac troponin I which was isolated had a molecular weight of 28 kDa. If the inhibitor concentration is reduced, increasing amounts of lower molecular weight components (24 kDa and lower by gel electrophoresis) are isolated, as well as the 28 kDa material. For example, a four-fold reduction of inhibitor concentration was found to yield approximately 80% of product as 28 kDa material.

The concentration of the inhibitors could be reduced even further depending upon the ultimate use of the troponin I and its stability requirements.

Cardiac troponin I prepared by the method of the present invention, having a molecular weight of 28 kDa, shows remarkable storage stability. As described in Example 4 and illustrated in FIG. 3, substantially pure human cardiac troponin I in accordance with the invention was stable at 4° C. or at room temperature for up to 5 weeks, thus providing a superior preparation for use as calibrators for cTnI assays and as standards for membrane-based or other matrix-based panel tests. These calibrators are necessary in order to standardize the test procedures in medical/hospital laboratories in order to ensure accurate and reproducible test results.

The purification procedure exemplified according to the present invention comprises the steps of extracting human cardiac tissue with an aqueous extraction buffer containing 8 to 10 M urea, and the protease inhibitor mixture of the present invention; separating the cardiac troponin I from the extract by affinity chromatography; and eluting the cardiac troponin I from the column matrix.

The cardiac tissue is first homogenised, using any number of known techniques, in an extraction buffer containing the mixture of protease inhibitors, as discussed above and 8 to 10 M urea. The extraction buffer can be any buffering system at a neutral to slightly basic pH, for example from a pH of 7.0 to 9.0. The extraction buffer can also contain other components, for example a reducing agent such as mercaptoethanol.

Once the tissue has been homogenised, the solid material is removed by any number of methods such as filtration or centrifugation. A filtration step through glass wool is useful to remove any lipid material. The cardiac troponin I can then be purified from the extract by column chromatography. In the present invention, rabbit skeletal muscle troponin C was coupled to a column matrix, for example an agarose gel matrix, in the presence of $Ca^{++}$. The rabbit skeletal muscle troponin C was prepared as described by Syska et al (FEBS Lett. (1974), vol 40, p.253). In one embodiment of the present invention the rabbit skeletal muscle troponin C was coupled to Sepharose-4B as described by Cummins et al. (Arm Heart J., (1987), vol. 113, p.1333). The column matrix, troponin C-sepharose gel, in the presence of calcium $Ca^{++}$ was contacted with the troponin extract. The Troponin I will specifically bind to the troponin C. Traditionally the gel is packed into a chromatography column and the cardiac troponin I is eluted using EGTA in the extraction buffer. It has, however, been found that a higher yield of troponin I can be obtained if it is purified using a batch procedure. In this procedure, the troponin I extract is mixed with the troponin C sepharose gel overnight. The cTnI is eluted using EGTA from the gel in the tubes without having to pack the matrix into a column.

Other methods are known in the art for the extraction and purification of troponin I. These methods have been described in general and can be found in detail in Beier et al., (1988) and Jin et at. (1988), and Stull et al., (1977), all of which are incorporated herein by reference. These methods can be used, except according to the present invention, one would use the present protease inhibitor mixture to improve the yield of stable, intact cardiac troponin I, which was not isolated using these prior an methods.

In addition, isolation of troponin I can also be improved using the proteases of the present invention from a heterologous expression system, in which a cDNA coding for cardiac troponin I is expressed in a suitable heterologous system, employing, for example, bacteria, insect, eukaryotic, or mammalian host cells.

The following examples are illustrative only and not intended as limiting with respect to the present invention.

EXAMPLE 1

Materials: Antipain, aprotinin, bestatin, 3,4 dichloro- isocoumarin, N-[N-(L-3-tram-carboxyoxiram-2-carbonyl)-L-leucyl]-agmatine (E-64), leupeptin, pepstatin A, phosphoramidone, chymostatin and PMSF were obtained from Sigma Chemical Company, St. Louis. HPlX? grade or the highest available purity was used.

Bestatin and pepstatin A were each dissolved in 100% MeOH at a concentration of 500 mg/L; 3,4 dichloro- isocoumarin was dissolved in DMSO or DMF at 500 mg/L; (E-64) was dissolved in Ethanol/water (1:1) at 500 mg/L; phenyl methyl sulphonyl fluoride (PMSF) was dissolved in 95% ethanol at 200 mM.

Aliquots of these stock solutions and appropriate weights of each of the remaining above-listed protease inhibitors were mixed with water to give a protease inhibitor stock solution containing 200 mM PMSF and 100 mg/L of each of the other above-listed protease inhibitors. This stock solution was diluted in Basic Buffer solution (9 M urea; 75 mM Tris-HCl; 1 mMCaCl$_2$; 60 mM 2-mercaptoethanol, pH 8.0) to give an Extraction Buffer containing 2 mM/L PMSF and 1 mg/L of each of the other above-listed protease inhibitors.

EXAMPLE 2

Human cardiac tissue was obtained from human cadavers. The tissue was homogenised in 10 volumes of Extraction Buffer (composition as in Example 1 ). The crude homogenate was then centrifuged at 10,000×g for 20 minutes. The supernatant was passed through glass wool to remove lipid and dialysed for 5 h at room temperature against Extraction Buffer. The dialysed supernatant was purified by affinity chromatography, using rabbit skeletal muscle troponin C prepared as described by Syska et al (FEBS Lett. (1974), vol 40, p.253) and coupled to Sepharose-4B as described by Gummira et al. (Am. Heart J., (1987), vol. 113, p.1333).

Although the entire dialysed supernatant may be incubated in bulk with the troponin C-Sepharose gel, it was found convenient to add 35 ml aliquots of dialised supernatant to 8 ml aliquots of rabbit troponin C-Sepharose gel in 50 ml capped centrifuge tubes. An additional amount of protease inhibitor mixture was added to the supernatant/gel mixture (a volume of protease inhibitor 100 mg/L stock solution of approximately 25% of volume of Extraction Buffer in initial tissue homogenisation) and binding was carried out overnight at 4° C. with shaking.

Figure 1:
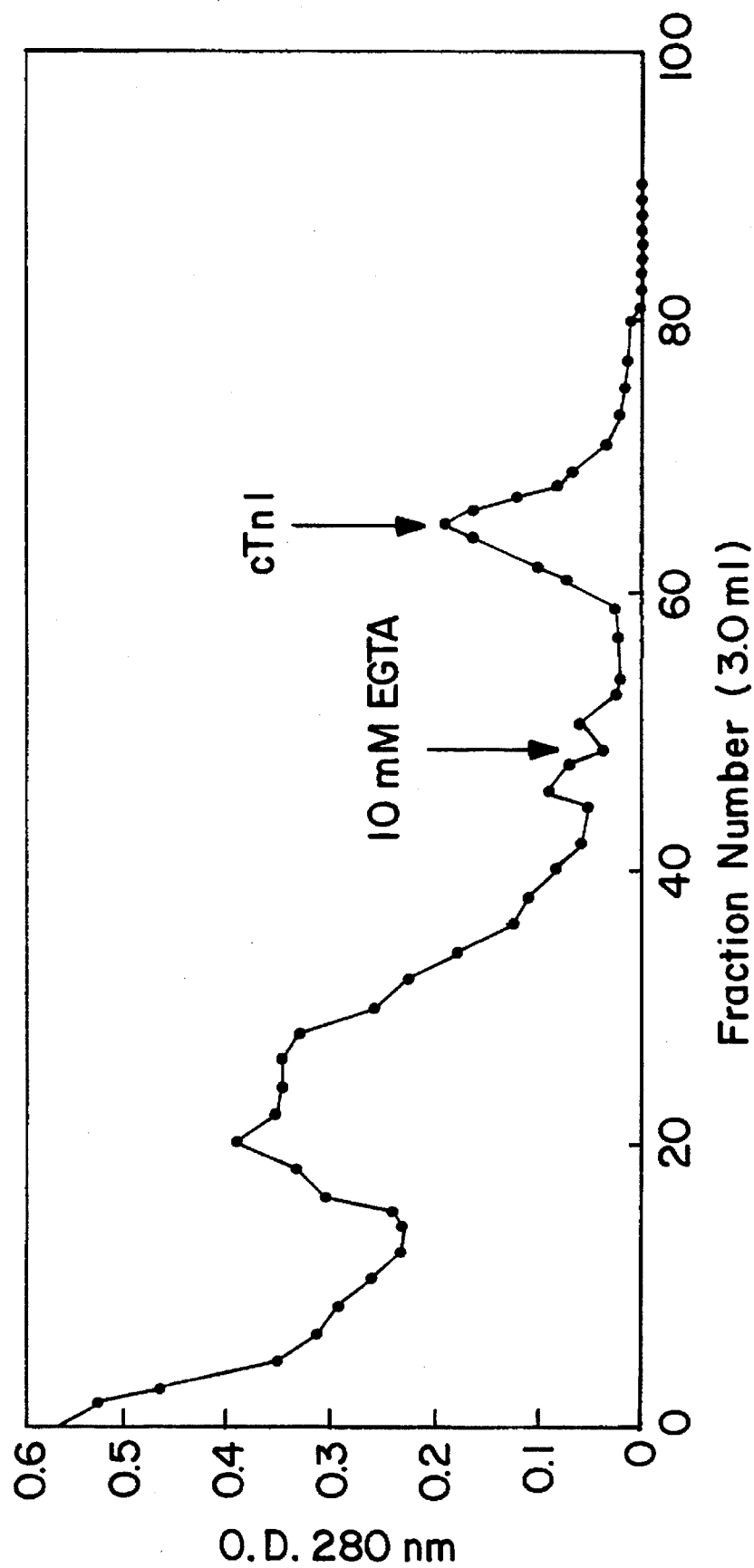
FIG. 1 shows the elution profile of cTnI prepared in accordance with one embodiment of the invention.

The gel was then packed into a chromatography column (1.5×10.0 cm) and unbound protein was washed out with Basic Buffer. Cardiac troponin I was then eluted as a single peak using 10 mM EGTA in Extraction Buffer. A typical elution profile is shown in FIG. 1.

The fractions containing cTnI were pooled and dialysed against 0.5 M NaCl, 20 mM Tris-HCl, 60 mM 2- mercaptoethanol, pH 7.5, overnight at 4° C. The dialysed cTnI was concentrated by ultrafiltration in an Amicon cell using a YM3 membrane (Amicon). Protein concentration was determined using an extinction coefficient of 4.2.

Alternatively, improved yields of troponin I were obtained using a batch procedure. In this method the cTnI is eluted from the gel in the tubes without having to pack the matrix into a column.

EXAMPLE 3

The homogeneity of cardiac troponin I prepared as in Example 2 was shown by the presence of a single band on SDS gel electrophoresis, carried out as described by Laemmli (1970), Nature, v. 227. pp. 680–685. A typical gel is shown in FIG. 2. The molecular weight of the cardiac troponin I prepared was 28 kDa which contrasts with the reported values of 22.5 kDa (Larue et al. (1992), Molecular Immunology, v. 29, pp. 271–278) and 24 kDa (Cummins et at. (1978) Biochem. J. v. 171, p. 251–257).

Omission of aprotinin and 3,4 dichloroisocoumarin from the inhibitor mixture did not destroy the protective effect and homogeneous 28 kDa cardiac troponin I was obtained.

Analysis showed that the purified cardiac troponin I had 6% glycosylation (data not shown).

Amino acid analysis of cardiac troponin I prepared as in Example 2 was carried out using the Pico-tag System (Bidlingmeyer et al., (1984), J. Chrom., v. 336, pp. 93–104; Cohen et al., (1988), Anal. Biochem., v. 174, pp. 1–16). The results are shown in Table 2.

Amino acid analysis of the substantially pure 28 kDa troponin I of the invention gave the values shown in Table 2, Column 1. Theoretical values based on the deduced amino acid sequence are shown in Column 2. Analysis of the 24 kDa material obtained when troponin I was isolated using lower protease inhibitor concentrations is also shown in Table 2 (Column 3). It is interesting that the amino acids which are most reduced in this 24 kDa material (Asp, Arg, Pro, Tyr) occur frequently in the cardiac-specific 31 amino acid N- terminal sequence of human cTnI (Vailins et al., (1990), FEBS Lett. v. 270, pp. 57–61), suggesting that this is the fragment lost from the 28 kDa intact protein.

TABLE 2

AMINO ACID ANALYSIS OF HUMAN cTnI

| Amino Acid | Column 1 28 kDa cTnI | Column 2 Theoretical | Column 3 24 kDa species |
|---|---|---|---|
| asp (+ asn) | 15 | 17 | 10 |
| glu (+ gln) | 30 | 30 | 24 |
| ser | 10 | 12 | 7 |
| gly | 10 | 10 | 9 |
| his | 3 | 3 | 2 |
| arg | 20 | 25 | 12 |
| thr | 7 | 9 | 6 |
| ala | 23 | 23 | 16 |
| pro | 8 | 7 | 4 |
| tyr | 3 | 3 | 1 |
| val | 6 | 6 | 5 |
| met | 0 | 4 | 0 |
| cys | 0 | 2 | 0 |
| ile | 7 | 9 | 5 |
| leu | 18 | 22 | 14 |
| phe | 3 | 4 | 2 |
| lys | 11 | 23 | 8 |
| trp | 0 | 1 | 0 |

Values are expressed as the nearest whole number of amino acid residues/molecule of protein based on apparent molecular weights of 28,000 for intact human cardiac troponin I and 24,000 for the degraded product. The results represent average of two determinations done on the same day. The values for columns 1 and 3 have been corrected by computer optimization to take into account the phosphorylation and glycosylation of the molecule based on a minimum M.W. of 24036.25 based on cDNA deduced sequence.

The cardiac specific 31 amino acid sequence from the N-terminus is as follows:

H$_2$N—Ala—Asp—Gly—Ser—Ser—Asp—Ala—Ala—Arg—Glu—Pro—Arg—Pro—Ala—Pro—
Ala—Pro—Ile—Arg—Arg—Arg—Ser—Ser—Asn—Tyr—Arg—Ala—Tyr—Ala—Thr—Glu—OH
(SEQ ID NO:1)

EXAMPLE 4

The stability of cardiac troponin I prepared as in Example 2 was examined under a variety of conditions, as described below. Integrity was assessed by homogeneity on SDS gel electrophoresis and also by ELISA in some cases.

Figure 3:
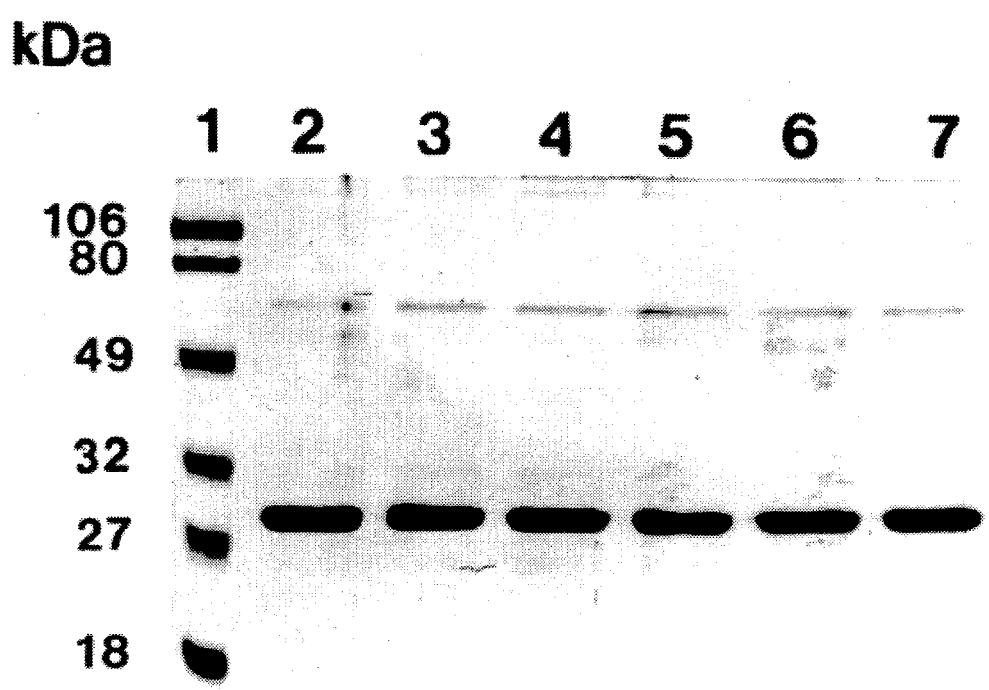
FIG. 3 shows the stability of human cTnI prepared by the method of the invention at 4° C., wherein, Lane 1: molecular weight standards (as in FIG. 2), Lanes 2–6: cTnI stored at 4° C. for
  Lane 2: 1 week
  Lane 3: 2 weeks
  Lane 4: 3 weeks
  Lane 5: 4 weeks
  Lane 6: 5 weeks, and Lane 7: control preparation of cTnI stored at –20° C.

(1) Cardiac troponin I was stored at 4° C. in 0.5 M NaCl, 20 mM Tris-HCl and 60 mM 2-mercaptoethanol, pH 7.5, at a concentration of 0.8 mg/ml, for up to five weeks. Aliquots were removed at various times over this period of storage and examined for homogeneity by SDS-PAGE. At all times, troponin I gave a single band of MW 28 kDa as seen in FIG. 3, which shows 1, 2, 3, 4 and 5 weeks of storage at 4° C.

(2) Cardiac troponin I was stored at −20° C. in buffer as in (1) above and was subjected to a thaw/refreeze cycle each day for 10 days. A single band on SDS-PAGE indicated that no significant degradation had occurred during this treatment (data not shown).

Figure 4:
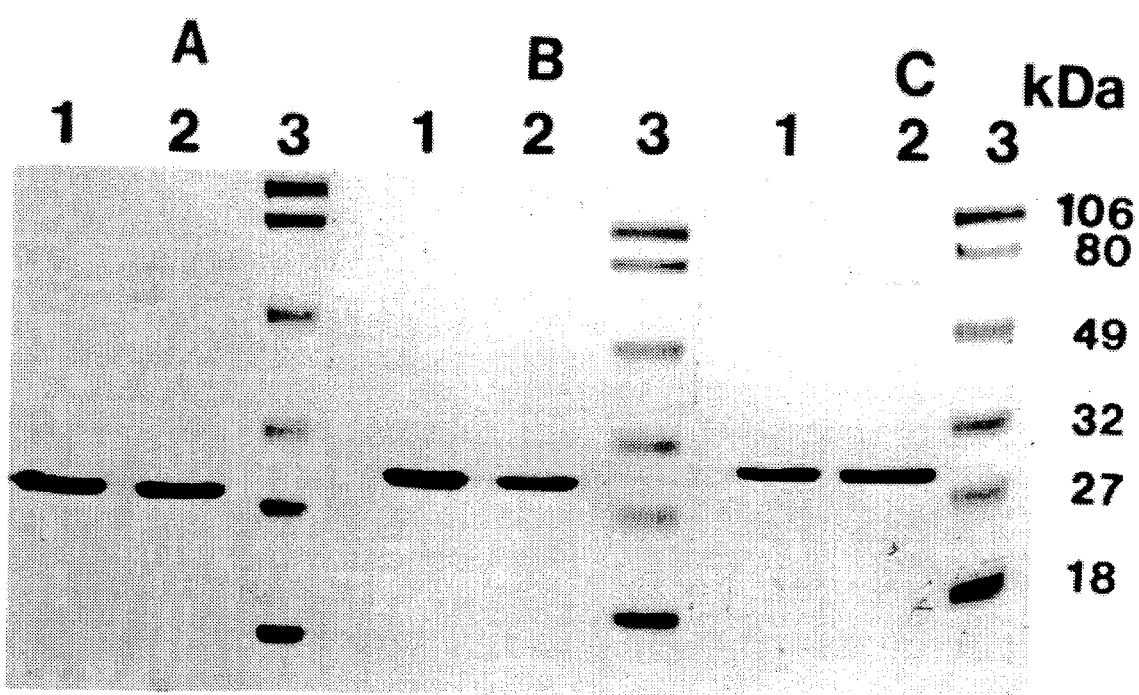

(3) Cardiac troponin I, in buffer as in (1) above, was stored at room temperature (approx. 22° C.) for up to 5 weeks. Aliquots were removed at various times over this storage period and assessed by SDS-PAGE. Troponin I stored at room temperature for up to 5 weeks showed no significant degradation, as seen in FIG. 4.

Examination of cardiac troponin I by ELISA after storage at 4° C. or room temperature showed no difference from fresh preparations.

All literature cited herein is specifically incorporated by reference.

The present invention is not limited to the features of the embodiments described herein, but includes all variations and modifications within the scope of the claims.

We claim:

1. A method of isolating a pure, stable cardiac troponin I preparation, the troponin I having a molecular weight of about 28 kDa, which comprises the steps of:

extracting human cardiac tissue with an aqueous extraction buffer at a pH of from about 7 to 9 which is 8 to 10 M in urea and contains a protease inhibitor mixture comprising at least two cathepsin protease inhibitors, at least one serine protease inhibitor and at least one cysteine protease inhibitor;

separating the troponin I from the extract by affinity chromatography in the presence of the extration buffer and calcium ions thereby to absorb the troponin I; and desorbing a troponin I by washing with the aqueous extraction buffer containing EGTA.

2. The method according to claim 1, wherein the protease inhibitor mixture further comprises at least one of the group consisting of: an aspartate protease inhibitor, an aminopeptidase protease inhibitor and a metalloendo-peptidase inhibitor.

3. The method according to claim 2, wherein the peptidase inhibitor mixture comprises leupeptin, pepstatin, phenylmethanesulfonyl fluoride (PMSF) and N-[N-(L-3-trans-carboxy-oxiram-2-carbonyl)-L-leucyl]-agmatine (E-64).

4. The method according to claim 3, wherein the protease inhibitor mixture comprises leupeptin, pepstatin, PMSF and E-64, pepstatin and phosphoramidon.

5. The method according to claim 4, wherein the protease inhibitor mixture comprises antipain, bestatin, E-64, leupeptin, pepstatin A, phosphoramidone, chymostatin and PMSF.

6. The method according to claim 5, wherein the protease inhibitor mixture comprises antipain, aprotinin, bestatin, 3,4 dichloro- isocoumarin, E-64, leupeptin, pepstatin A, phosphoramidone, chymostatin and PMSF.

7. The method according to claim 1, wherein the protease inhibitor mixture is effective to inhibit degradation of the N-terminal region of the cardiac troponin I.

8. The method according to claim 7, wherein the N-terminal sequence of cardiac troponin I includes a 31 amino acid N-terminal sequence of cardiac troponin I (SEQ ID NO: 1).

9. The method according to claim 1, wherein the protease inhibitor mixture is present in a 9 molar urea solution.

10. The method according to claim 1, wherein the protease inhibitors are used at a concentration ranging from 0.25 mg/l to 1 mg/l or 0.05 mM to 2 mM if the protease inhibitor is PMSF.

11. The method according to claim 1 wherein the extraction buffer is a 75 mM Tris-HCl buffer, pH 8.0.

12. The method according to claim 11, wherein the extraction buffer further contains 1 mM $CaCl_2$ and 60 mM mercaptoethanol.

13. The method according to claim 1, wherein rabbit skeletal muscle troponin C coupled to an agarose gel matrix, in the presence of calcium ions is used to affinity purify the cardiac troponin I.

* * * * *